(12) United States Patent
Zornberg et al.

(10) Patent No.: US 7,367,218 B2
(45) Date of Patent: May 6, 2008

(54) CENTRIFUGE PERMEAMETER FOR UNSATURATED SOILS SYSTEM

(75) Inventors: Jorge G. Zornberg, Austin, TX (US); John S. McCartney, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 51 days.

(21) Appl. No.: 11/563,052

(22) Filed: Nov. 24, 2006

(65) Prior Publication Data

US 2007/0131023 A1  Jun. 14, 2007

Related U.S. Application Data

(62) Division of application No. 11/563,053, filed on Nov. 24, 2006, and a division of application No. 11/297,261, filed on Dec. 8, 2005.

(60) Provisional application No. 60/634,189, filed on Dec. 8, 2004.

(51) Int. Cl.
*G01N 15/08* (2006.01)
(52) U.S. Cl. .......................................................... 73/38
(58) Field of Classification Search .................. 73/37, 73/38
See application file for complete search history.

(56) References Cited

U.S. PATENT DOCUMENTS

| 4,679,422 A | 7/1987 | Rubin et al. .................... 73/38 |
| 6,055,850 A | 5/2000 | Turner et al. ................... 73/38 |
| 6,571,605 B2 | 6/2003 | Johnson ......................... 73/38 |
| 6,634,876 B2 | 10/2003 | Osugi et al. ................. 418/260 |
| 6,665,192 B2 | 12/2003 | Wimberger Friedl et al. .......................... 361/752 |
| 6,810,755 B1 | 11/2004 | Pask et al. ..................... 73/863 |
| 6,935,159 B2 * | 8/2005 | Knight et al. ................... 73/38 |
| 2005/0177309 A1 * | 8/2005 | Sri Ranjan et al. ............. 702/2 |

* cited by examiner

*Primary Examiner*—Hezron Williams
*Assistant Examiner*—Tamiko Bellamy
(74) *Attorney, Agent, or Firm*—Edwin Flores; Chalker Flores, LLP

(57) ABSTRACT

The present invention includes an apparatus, method and centrifuge permeameter system that includes a hydraulic permeameter adapted for use in a centrifuge; and an automated data acquisition system, wherein the centrifuge permeameter non-destructively determines one or more soil characteristics from a sample of granular material such as soil, rock, and concrete when centrifuged.

7 Claims, 7 Drawing Sheets

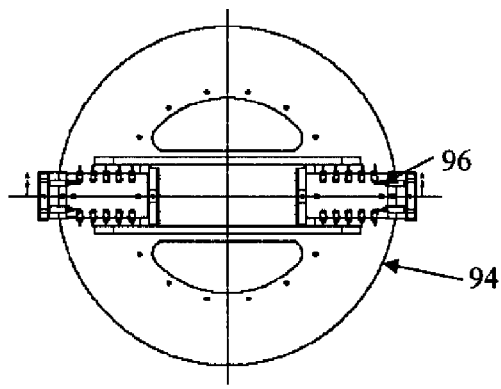
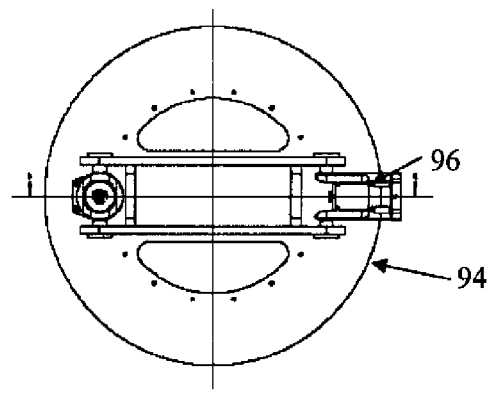
FIGURE 7A  FIGURE 7B
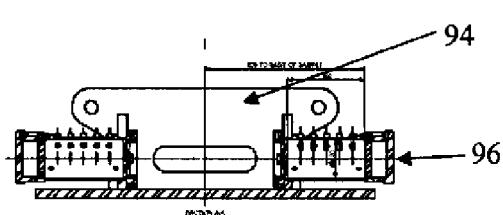
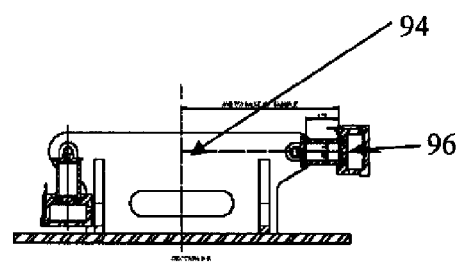
FIGURE 7C  FIGURE 7D
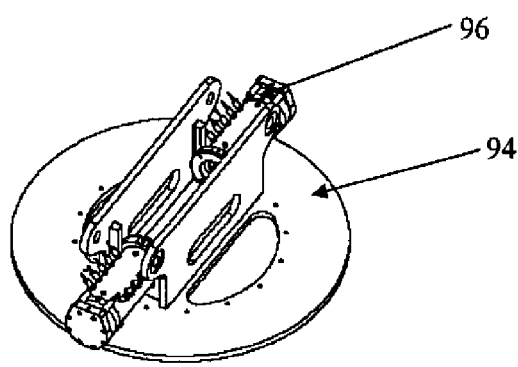
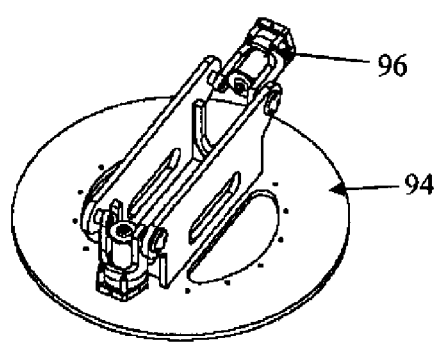
FIGURE 7E  FIGURE 7F

CENTRIFUGE PERMEAMETER FOR UNSATURATED SOILS SYSTEM

CROSS-REFERENCE TO RELATED APPLICATIONS

This application claims the benefit of U.S. Provisional Application Ser. No. 60/634,189, filed Dec. 8, 2004, the contents of which are incorporated by reference herein in their entireties. This application is a Divisional Application of U.S. patent application Ser. No. 11/297,261, filed Dec. 8, 2005 and Divisional Application U.S. patent application Ser. No. 11/563,053, also filed Nov. 24, 2006.

This invention was made with U.S. Government support under Contract No. CMS-0094007 awarded by the NSF. The government may own certain rights in this invention. Without limiting the scope of the invention, its background is described in connection with soil permeameters.

TECHNICAL FIELD OF THE INVENTION

The present invention relates in general to the field of permeameters, and more particularly, to a centrifuge permeameter that allows continuous, non-destructive and non-intrusive measurements of relevant variables.

BACKGROUND OF THE INVENTION

For example, U.S. Pat. No. 4,679,422, issues to Rubin, et al., discloses a method and apparatus for steady-state measurement of liquid conductivity in porous media. U.S. Pat. No. 6,634,876, issued to Schofield, discloses centrifuges and associated apparatus and methods.

U.S. Pat. No. 6,810,755, issued to Pask, et al., for a permeameter system and method to determine soil hydraulic capacity for onsite wastewater systems. The permeameter has a hollow tube with a second tube slidably disposed within an internal chamber of the hollow tube and is used in combination with one or more tables to correlate a specific rate of reading fall rate of water to the soil hydraulic capacity of the soil being tested. A conventional measuring tape is affixed to the outside surface of the hollow tube such that the numbers extend vertically along the length, or longitudinal central axis, of the hollow tube. The permeameter is used in combination with one or more charts that correspond with soil hydraulic capacity. The charts are created by formulas defined using known soil absorption principals, the dimensions of the permeameter, the dimensions of an auger hole in the soil, and the level of a water line in the auger hole.

Another permeameter is taught in U.S. Pat. No. 6,571,605, issued to Johnson. Johnson teaches a constant-head soil permeameter for determining the hydraulic conductivity of earthen materials. The constant-head soil permeameter is used to determine hydraulic conductivity of earthen materials in a borehole. The permeameter uses includes a calibrated reservoir attached to a suitable length of hose. Water is added to the calibrated reservoir and allowed to flow freely into until an equilibrium level is reached in the borehole and inside the soil permeameter. The water flowing to the permeameter is throttled by buoyant float pressure, thereby allowing better constant head control and much greater depths of testing than previously attained by known permeameters. The permeameter may also include a filtered vent system, backflow check valve, and seals. The filter system restricts entry of soil particles and debris, thereby minimizing cleaning and maintenance of the invention. The soil permeability is determined based on the equilibrium height of water, rate of water flow, and dimensions of the borehole.

Yet another permeameter is taught in U.S. Pat. No. 6,655,192, issued to Chavdar for a combined permeameter-porosimeter that measures normal and lateral permeability measurements on porous materials. The permeability measurements may be taken from compressed or uncompressed samples at room or elevated temperatures. A wide variety of fluids or gas may be used to penetrate the test fluid depending on the application and the porosity of the sample. Briefly, the penetrating test fluid is forced through the sample under pressure and the load, the fluid displacement, and the time are used to calculate the permeability, porosity, pore size distribution, average pore size and the number of pores per unit area.

Finally, U.S. Pat. No. 6,055,850, issued to Turner, et al., teaches a multi-directional permeameter that is used to determine the coefficients of permeability using a constant (or falling) head method for the laminar flow of a fluid (e.g., water), through a specific material or test sample. The apparatus is a mold secured to a base, a lid is secured to the mold, inlet and outlet ports allow fluid flow to occur in both the horizontal plane and the vertical plane to determine the coefficients of permeability of a particular sample either horizontally, vertically, or simultaneously horizontally and vertically.

SUMMARY OF THE INVENTION

The present invention is an apparatus, method and system for a centrifuge permeameter that allows continuous, non-destructive, and non-intrusive measurement of relevant hydraulic variables (suction, moisture content, fluid flow rate) in a single specimen while in-flight in the centrifuge. The centrifuge permeameter allows a user to obtain an accelerated definition of the fluid retention curve and hydraulic conductivity function, simultaneously. The present inventors recognized that current testing methods used to define the unsaturated hydraulic properties often require the use of several specimens, significant testing times, and destructive or intrusive measurement of the variables.

Furthermore, it was found that available technologies do not allow determination of the fluid retention curve and hydraulic conductivity function simultaneously. Also, current centrifuge technology does not allow the direct acquisition of the relevant variables (e.g., suction, moisture content, fluid flow rate) in-flight during testing. The time-consuming nature of current conventional technology and its effect on test data, results in inefficient use of resources and limited usefulness for the data gathered.

For example, determination of the hydraulic properties for a low-permeability clay specimen may take over one year (more than one month for each data-point in either the fluid retention curve or hydraulic conductivity function). Penneability information is obtained in a few days with the centrifuge permeameter disclosed herein.

The present invention permits the simultaneous determination of the fluid retention curve and hydraulic conductivity function for soil, rock, or concrete. Overall, the apparatus, system and method may be used for low-hydraulic conductivity materials, the hydraulic properties of which cannot be obtained in a practical manner using currently available technology. In addition, the apparatus, system and method encourages the use of experimentally obtained hydraulic properties for practical problems, instead of the currently used analytical predictions.

The present invention includes a centrifuge permeameter system and method of use in which a hydraulic permeameter is adapted for use in a centrifuge and is in communication with an automated data acquisition system that detects one or more soil characteristics from a soil sample connected to the hydraulic permeameter. The automated data acquisition system non-destructively determines one or more soil characteristics from a soil sample of porous material such as soil, rock, and concrete when centrifuged. The one or more soil characteristics may be selected from variables including: suction, moisture content, hydraulic conductivity and the relationship between one or more of these variables. Examples for use of the permeameter include geotechnical engineering (e.g., fluid flow and mechanical analyses), hydrology (e.g., groundwater recharge calculations), agriculture (e.g., plant-soil interaction analysis), environmental engineering (e.g., contaminant transport analyses), and petroleum engineering (e.g., oil reservoir characterization).

The permeameter is designed to control the inflow and outflow boundary conditions to generate open-flow boundary conditions that do not interfere with the ongoing flow process. Generally, the inflow and outflow boundary conditions will not impose a suction value onto the specimen. Furthermore, the one or more inflow boundary condition and one or more outflow boundary condition may be selected to permit the suction and moisture content to attain any value in equilibrium with an ongoing flow process controlled by a fluid flow rate imposed on the sample. The permeameter instrumentation may continuously and nondestructively measure one or more variables relevant to unsaturated fluid flow through soils while the centrifuge is in flight. Examples of the values that the automated data acquisition system may continuously measure include, e.g., one or more of the following: moisture content, suction, temperature, relative humidity, specimen weight and combinations or variations thereof.

Another embodiment of the invention is a centrifuge permeameter system with an automated data acquisition system for measuring unsaturated soil characteristics that includes a permeameter that applies a fluid flow rate less than the saturated soil hydraulic conductivity to at least one portion of a soil specimen and controls the inflow and outflow boundary conditions to generate open-flow boundary conditions. The one or more soil characteristics is selected from variables including suction, moisture content and hydraulic conductivity and from the relationship between these variables and may be used for fluid flow and mechanical analyses, groundwater recharge calculations, plant-soil interaction analyses, contaminant transport analyses and oil reservoir characterization.

The present invention also includes a method of measuring unsaturated soil characteristics by placing a soil sample in a centrifuge permeameter, applying a centripetal acceleration to the soil specimen, applying a low-flow rate to at least one side of the soil specimen during centrifugation, controlling inflow and outflow boundary conditions within the permeameter to generate open-flow boundary conditions; and continuously measuring one or more characteristics of the soil sample while in flight. The centripetal acceleration applied to the soil specimen is selected to permit the suction and moisture content to attain equilibrium with an ongoing flow process. Generally, the inflow and outflow boundary conditions in the permeameter are selected to permit the suction and moisture content to attain any value in equilibrium with the ongoing flow processes. The permeameter will continuously and/or nondestructively measure the variables relevant to unsaturated fluid flow through soils, while the centrifuge is in flight.

Another embodiment of the present invention is a permeameter made from a cylinder having at least one window for visual inspection positioned between an inflow end of the cylinder and an outflow end of the cylinder. A fluid distribution cap is disposed at the inflow end of the cylinder and a porous sample support cap disposed at the outflow end of the cylinder and one or more primary outflow fluid collection reservoirs disposed within the cylinder. The one or more primary outflow fluid collection reservoirs are disposed about the cylinder includes one or more pore water pressure transducers to measure outflow volume within the cylinder; and a pinhole at the outflow reservoir to prevent build-up of air pressures in the outflow reservoir. The permeameter is adapted to operation within a centrifuge. The permeameter may also include one or more ports disposed about the cylinder to permit contact between the one or more ports and the soil sample to measure a suction profile.

The permeameter may also include one or more time domain reflectometry (TDR) probes at least partially within or about the cylinder to measure the average moisture content in the soil sample. In one embodiment, the permeameter is supported within the centrifuge on one or more weighing devices that monitor the weight of the permeameter. The centrifuge permeameter may also include a secondary overflow outflow fluid collection reservoir disposed in communication with the one or more primary outflow fluid collection reservoirs having one or more pressure transducers to measure outflow volume and a pinhole at the reservoir to prevent build-up of air pressures in the outflow reservoir. The permeameter instrumentation continuously and/or non-destructively measures one or more variables relevant to unsaturated fluid flow through soils while the centrifuge is in flight.

BRIEF DESCRIPTION OF THE DRAWINGS

For a more complete understanding of the features and advantages of the present invention, named the Centrifuge Permeameter for Unsaturated Soils (CPUS), reference is now made to the detailed description of the invention along with the accompanying figures in which:

FIGS. 7A to 7F show top and isometric views of the CPUS permeameter arrangements in the centrifuge.

DETAILED DESCRIPTION OF THE INVENTION

Figure 1A:
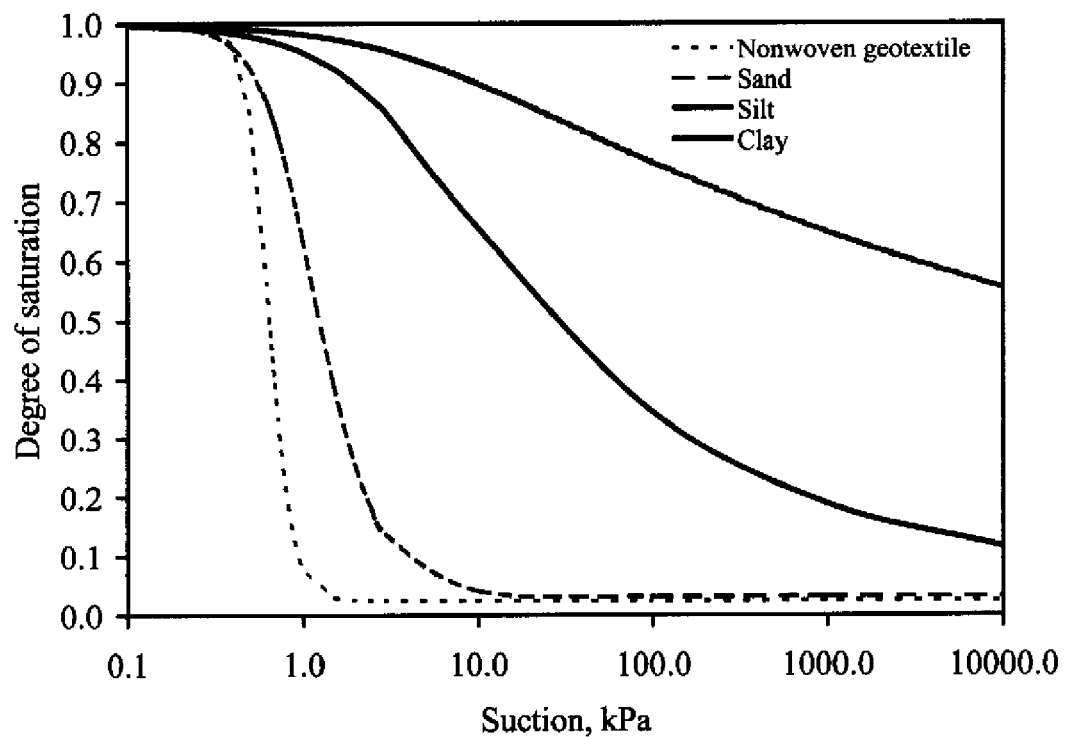
FIG. 1A is a graph of the fluid retention curves for different soils.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "prototype" denotes the scaled relationship between a small-scale specimen in the centrifuge and a large-scale earthen structure in the nature (e.g., dams, embankments, landfills, slopes, etc.).

The present invention is an apparatus, method and system for determining the hydraulic properties of porous materials. As mentioned, the system is a Centrifuge Permeameter for Unsaturated Soils (CPUS). The Centrifuge Permeameter is used to define the unsaturated hydraulic properties of porous materials such as soil, rock, and concrete.

The present invention provides a centrifuge permeameter system having a permeameter adapted for use in a centrifuge and an automated data acquisition system. The automated data acquisition system may be used to detect one or more soil characteristics from a soil sample connected to the hydraulic permeameter. The automated data acquisition system may include a CPU or a computer and may store data internally or externally and/or the data may be displayed or printed. The automated data acquisition system may be connected to other systems, main frames, printers, plotters or storage devices via direct connections, wifi connections, Bluetooth connections, IR connections, laser connections or other communication mechanism. In addition to the recording and processing of data by the automated data acquisition system, it may be used to control other parameters of the present invention.

The centrifuge permeameter non-destructively determines one or more soil characteristics from a sample of porous material such as soil, rock, and concrete when centrifuged. The one or more soil characteristics may include suction, moisture content, hydraulic conductivity and the relationship between these variables and the permeameter controls the inflow and outflow boundary conditions to generate open-flow boundary conditions by applying a fluid flow rate to at least one side of a soil specimen. Additionally, the permeameter further includes a fluid inflow distribution cap that does not impose a suction value onto the specimen. The inflow and outflow boundary condition are selected to permit the suction and moisture content to attain specific values at equilibrium, with an ongoing flow process that is controlled by a fluid flow rate imposed on the sample. The automated data acquisition system may continuously measures one or more values, e.g., moisture content, suction, temperature, relative humidity, fluid inflow rate, fluid outflow rate, specimen weight and combinations thereof.

A method of measuring unsaturated soil characteristics is also provided. A soil specimen is placed in a centrifuge permeameter and a centripetal acceleration to the soil specimen. A low-flow rate is applied to at least one side of the soil specimen during centrifugation and the outflow boundary conditions within the permeameter are controlled to generate an open-flow boundary condition. The characteristics of the soil specimen are continuously measured while in flight.

The automated data acquisition system continuously measures one or more soil characteristics from an unsaturated soil specimens, e.g., moisture content, suction temperature, fluid inflow rate, fluid outflow rate, steady-state fluid flow, specimen weight, evaporation and combinations thereof. The centripetal acceleration applied to the soil specimen is selected to permit a suction and a moisture content to attain equilibrium with an ongoing flow and the inflow and outflow boundary conditions in the permeameter permit the suction and moisture content to attain any value in equilibrium with the ongoing flow processes. Dry air or heat may be applied to the soil specimen to induce moisture evaporation while continuously and nondestructively measuring relevant variables such as the change in temperature, relative humidity, and small changes in the weight of a soil specimen while in flight.

The present invention also provides a permeameter adapted to operate within a centrifuge. The permeameter includes a cylinder having at least one window for visual inspection positioned between an inflow end of the cylinder and a outflow end of the cylinder. A fluid distribution cap is disposed at the inflow end of the cylinder and a porous sample support cap is disposed at the outflow end of the cylinder. The permeameter includes a primary fluid outflow collection reservoirs disposed about the cylinder which has one or more fluid pressure transducers to measure outflow volume and a pinhole to prevent build-up of air pressure in the outflow reservoir. The centrifuge permeameter of also includes two or more ports disposed about the cylinder to permit contact between one or more heat dissipation units (HDU) probes and the soil sample to measure a suction profile and/or one or more time domain reflectometry (TDR) probes at least partially within, the cylinder to measure the average moisture content in the soil sample.

Figure 1B:
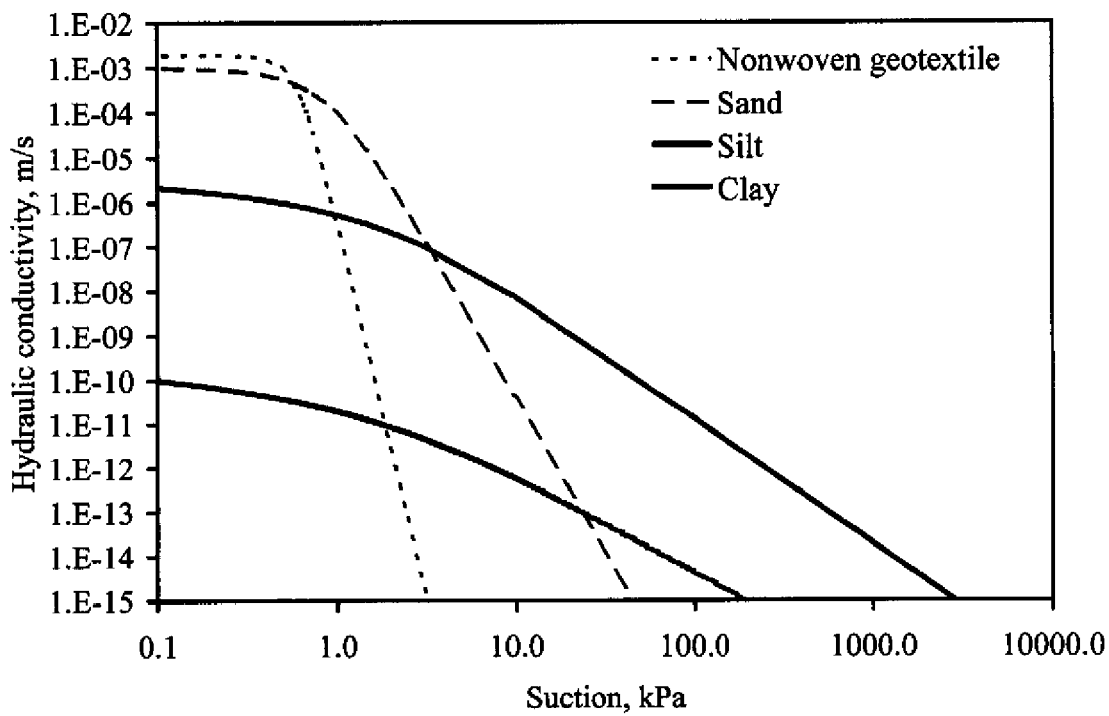
FIG. 1B is a graph of the hydraulic conductivity functions for different soils.

Unsaturated hydraulic properties include the relationships between suction and moisture content (the fluid retention curve), and suction and hydraulic conductivity (the K-function), examples of which are shown in FIGS. 1A and 1B for different porous materials. FIG. 1A is a graph that shows the fluid retention curve for different materials and FIG. 1B is a graph that shows the K-functions for different materials, which are determined concurrently, in flight using the present invention.

These properties are necessary information in several fields, including geotechnical engineering (fluid flow and mechanical analyses), hydrology (groundwater recharge calculations), agriculture (plant-soil interaction analysis), environmental engineering (contaminant transport analyses), and petroleum engineering (oil reservoir characterization.) The Centrifuge Permeameter incorporates the use of a low-flow hydraulic permeameter and a centrifuge to obtain these important material properties. The hydraulic permeameter is able to control the fluid flow rate and boundary conditions within a material specimen. By placing a specimen within the hydraulic permeameter under a centripetal acceleration in the centrifuge (which may be considered to be an increased gravitational field), the driving force for fluid flow rate is increased, which results in a quadratic decrease in the time required to reach steady-state fluid flow conditions. Consequently, the unsaturated hydraulic properties such as the fluid retention curve and the K-function can be obtained from a single specimen in a comparatively short period of time. An important feature of the Centrifuge Permeameter is that the relevant variables (suction, moisture content, fluid flow rate) are obtained continuously while testing the specimen in-flight within the centrifuge. This permits measurement of transient flow processes without changing the acceleration field (i.e., by stopping the centrifuge) in order to make measurements.

The Centrifuge Permeameter allows continuous, non-destructive, and non-intrusive measurement of all relevant variables (suction, moisture content, fluid flow rate) in a single specimen while in-flight in the centrifuge, to obtain an accelerated definition of the fluid retention curve and K-function simultaneously. Current testing methods used to define the unsaturated hydraulic properties often require the use of several specimens, significant testing times, and destructive or intrusive measurement of the variables. Also, available technologies do not allow determination of the fluid retention curve and hydraulic conductivity function simultaneously. Current centrifuge technology does not allow the direct acquisition of the relevant variables (suction, moisture content, fluid flow rate) in-flight during testing. The time-consuming nature of current conventional technology must be stressed. For example, determination of the hydraulic properties for a low-permeability clay specimen may take over one year (more than one month for each data-point in either the fluid retention curve or K-function). The same level of detailed information may be obtained in a few days with the Centrifuge Permeameter disclosed herein.

The CPUS system is characterized by being able to continuously measure the variables relevant to unsaturated fluid flow through soils while the centrifuge is in-flight. These variables include moisture content ($\theta$), suction ($\Psi$), temperature (T), inflow fluid flow rate, fluid outflow rate, and specimen weight. These variables have been successfully measured using a prototype permeameter under 1-g and under N-g in the centrifuge. The first three variables ($\theta$, $\Psi$ and T) are measured using currently available equipment (e.g., time domain reflectometry probes, heat dissipation units, and thermocouples, respectively). The centrifuge component of the CPUS system has a data acquisition system, discussed later, has the capability of monitoring these variables continuously.

In addition, CPUS system is characterized by applying a fluid flow rate to one side of a specimen and by properly controlling the inflow and outflow boundary conditions at the top and bottom of the permeameter. A particular set of boundary conditions are used in this system, referred to as open-flow boundary conditions. These boundary conditions permit the suction and moisture content to achieve equilibrium while controlling fluid flow processes. This is in contrast to fixed boundary conditions that maintain a particular value of suction or moisture content at the top and bottom of the permeameter.

The fluid inflow rate may be under the control of an infusion pump (not shown), and a low-flow hydraulic rotary fluid union that passes the fluid from the stationary environment to the spinning centrifuge environment. The minimum and maximum flow rates for the infusion pump are about 1 to about 100 ml/hr. A rotary fluid union is necessary because conventional flow pumps cannot be used within a centrifuge due to the high gravity forces and space limitations. In addition, the location of the pump outside the centrifuge allows direct monitoring of the fluid inflow rate and total volume infused. A peristaltic pump is also available for this application, which has a minimum flow rate is 0.18 ml/hr and a maximum flow rate of 200 ml/hr. However, an infusion pump is more suitable for use with a low-flow hydraulic rotary fluid union as the peristaltic pump has a pulsating flow rate. The skilled artisan will recognize that other pumps may be used for this application, which have a minimum flow rate of 0.1 ml/hr and a maximum flow rate of 300 ml/hr.

Figure 2A:
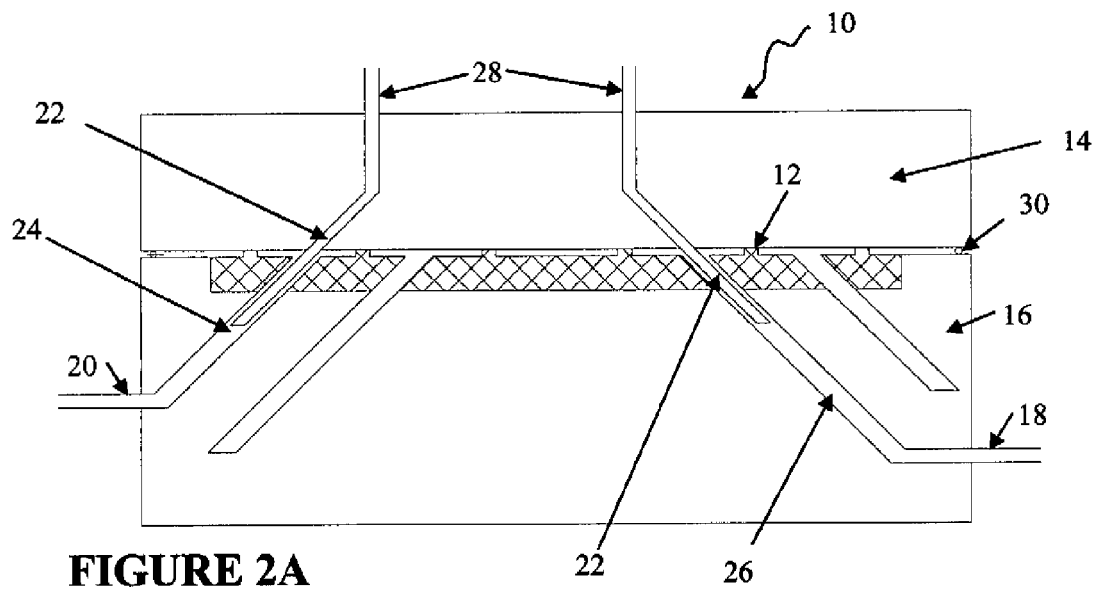
FIGS. 2A and 2B show the details of a rotary fluid union.

FIG. 2A shows a cross sectional view of the rotary fluid union with an interface 12 that connects an upper chamber 14 (also referred to as a stationary body), a lower chamber 16 (also referred to as a rotating body) and first fluid port 18 and second fluid port 20. The upper chamber 14 has two steel needles 22, while the lower chamber 16 has two angled concentric channels the first concentric channel 24 and the second concentric channels 26. The lower chamber 16 is free to rotate around the steel needles 22. Hydraulic lines (not shown) from the infusion pump (not shown) are connected to the two inflow lines 28 at the top of the rotary fluid union. Fluid moves into the steel needles 22 attached to the upper chamber 14, then drips into the two angled concentric channels 24 and 26 in the lower chamber 16. The fluid is conveyed via hydraulic lines (not shown) from the rotary fluid union to the permeameter by centripetal force. Interface seals (not shown) are provided to prevent fluid from moving from one of the two angled concentric channels 24 and 26 to the other. The upper chamber 14 and the lower chamber 16 may be in contact through one or more bearings 30; however, other interfaces may be used to allow movement of the chambers.

Figure 2B:
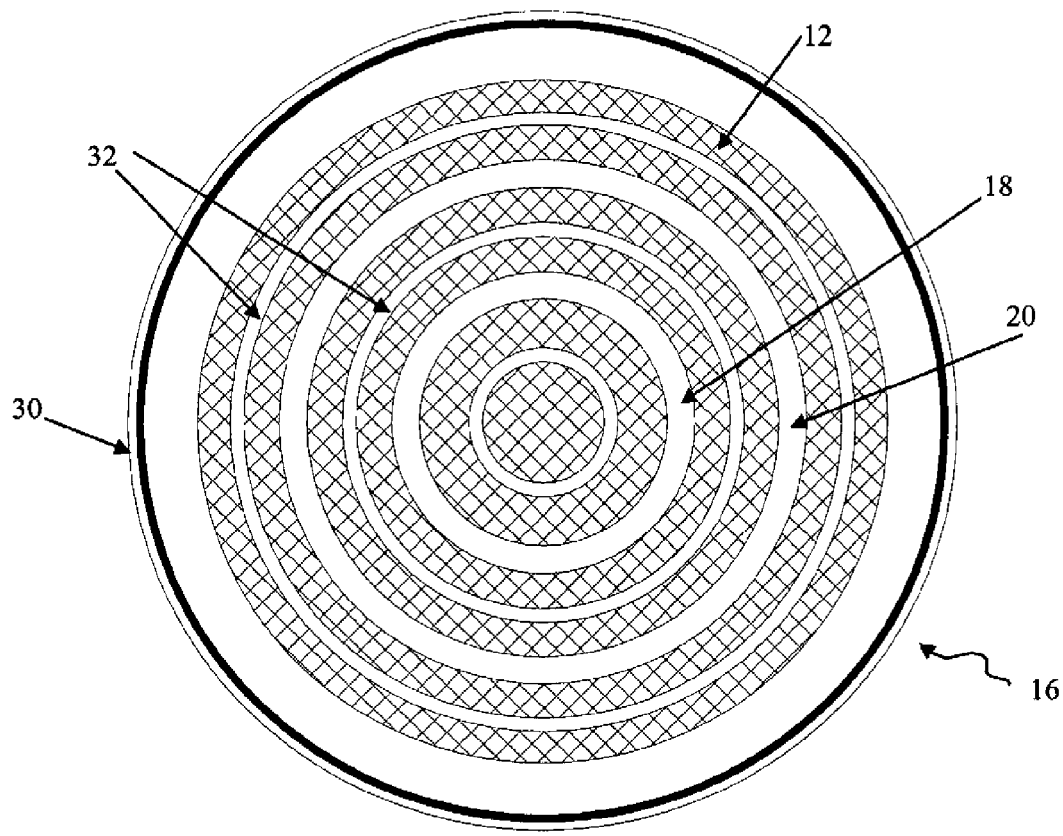

FIG. 2B is a top view of the lower chamber 16 of the rotary fluid union. FIG. 2B shows the rotary fluid union with an interface 12 that connects an upper chamber (not shown), a lower chamber 16 (also referred to as a rotating body) and the first fluid port 18 and the second fluid port 20. The first fluid port 18 and second fluid port 20 are separated by one or more drainage channels 32. Although, FIG. 2B depicts a single drainage channel 32 between each of the first fluid port 18 and second fluid port 20, the number of drainage channels 32 and the number of first fluid ports 18 and second fluids port 20 may vary. In one embodiment, the upper chamber (not shown) and the lower chamber 16 are made of stainless steel or other like materials and the interface 12 may be a low-friction, low heat-generating material, e.g., PolyTetraFluoroEthylene or sintered graphite. The skilled artisan will recognize that the materials may be varied depending on the particular needs of the specific application. For example, the upper chamber 14 and the lower chamber 16 may be constructed of in part or entirely of metals or alloys, e.g., copper, brass, iron, steel, chromolly, aluminum, etc. In addition, the upper chamber 14 and/or the lower chamber 16 may be constructed of layers of materials, e.g., stainless steel layer on top of a aluminum layer on top of another stainless steel layer or a fiberlayer (e.g., carbon fiber or fiberglass) layer under a metal layer. The materials may also be coated in some applications. Coating may be used to protect the parts, provide a non stick surface, provide a textured surface, etc.

Figure 3C:
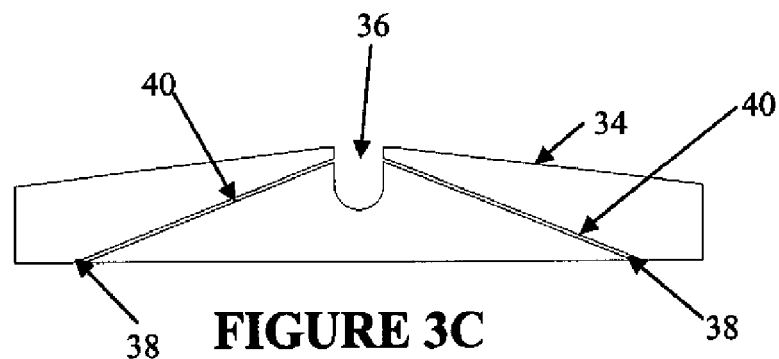
FIGS. 3A to 3C show the details of an inflow fluid distribution cap.
Figure 3B:
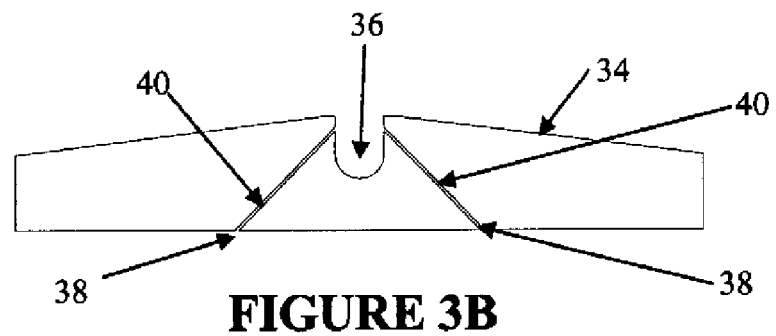
Figure 3A:
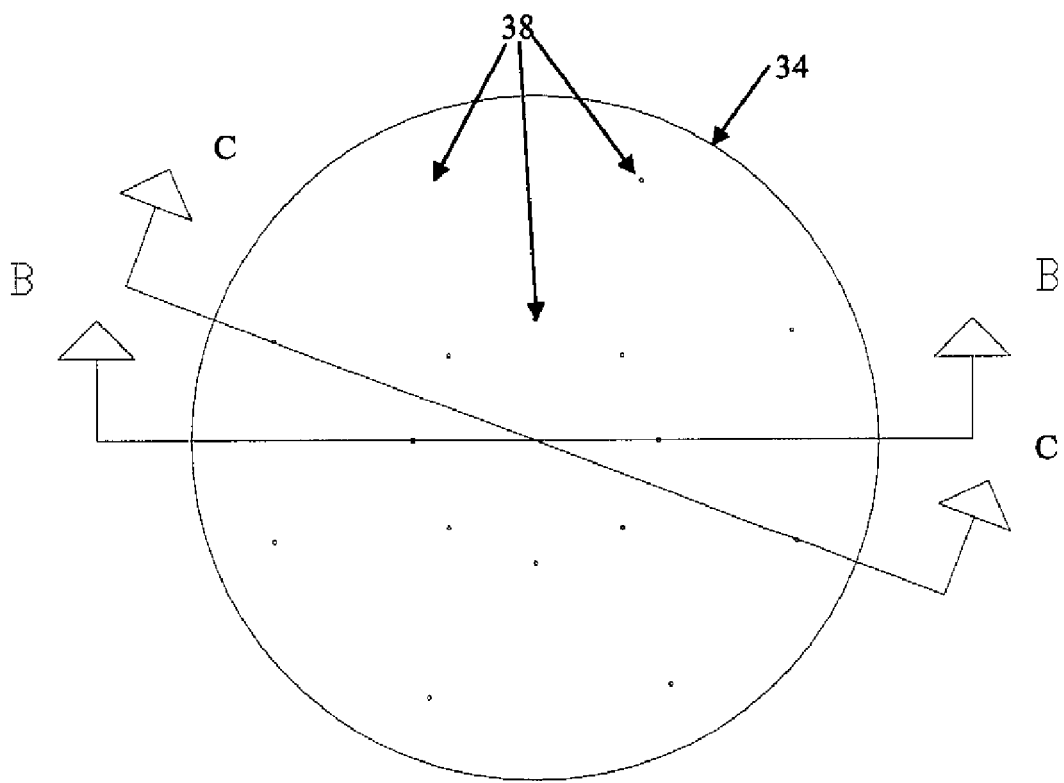

FIG. 3A is a bottom view of the inflow distribution cap 34. The upper boundary for the CPUS permeameter is a fluid inflow distribution cap 34, which ensures even distribution of fluid inflow to the top boundary of the specimen inside the permeameter. A hydraulic connection (not shown) consisting of plastic or flexible metal piping connects the low flow fluid union to the inflow distribution cap 34. The fluid flows into the reservoir (not shown) to a series of holes 38. The number and position of the individual holes in the series of holes 38 may be varied depending on the application.

FIGS. 3B and 3C show cross section views of the fluid inflow distribution cap 34. Fluid flows into the reservoir 36 at the top of the inflow distribution cap 34 and then overflows from this reservoir 36 into the series of holes 38 through a series of reservoir channels 40. These series of holes 38 are angled from the reservoir 36 to different locations on the bottom of the inflow distribution cap 34.

Furthermore, the dimensions of the present device vary depending on the particular application. For example, the lower boundary for the CPUS permeameter may be about 0.5 inch thick steel or acrylic supporting disc with a honeycomb pattern of 1/32 inch holes; however, other dimensions may be used, e.g., the CPUS permeameter may be between about 0.1 and 1 inch thick or greater than one inch thick and the holes may be between about 1/64 and about 1 inch. Furthermore, the holes do not need to be of a uniformed size over the surface and may be varies and alternated as needed. The inflow distribution cap 34 may be overlain by a porous filter paper or a wire mesh to prevent clogging.

A shallow-sloped funnel (not shown) beneath the supporting disc (not shown) will drain fluid to a small hole (not shown) that leads to a collection reservoir (not shown). The amount of fluid in the collection reservoir (not shown) (i.e., the outflow) is measured using a pressure transducer (not shown). This is possible because the fluid pressure at the base of the collection reservoir (not shown) is related to the height of fluid in the collection reservoir (not shown), implying that the volume can be calculated from the fluid pressure (see FIGS. 5 and 6, herein below). For redundancy, the outflow collection reservoir may be removed and weighed.

The CPUS system may also measure small changes in the weight of the specimen for measurement of evaporation (not shown). Two methods have been developed: a load cell system and a device based on the principle of a manometer. Briefly, the connection between the permeameter and the centrifuge rests upon an electronic load cell or a piston that transmits the weight of the specimen to a column of a dense fluid (e.g., mercury). The fluid column is calculated to have the same initial mass as the original specimen (before fluid flow occurs). Accordingly, small changes in weight of the specimen within the permeameter due to evaporation are inferred by the electronic load cell or by how much the piston moves the column of mercury, with the pressure in the mercury measured using a pressure transducer.

The following discussions provide technical details for different permeameters that are used in the CPUS system. These include a shrink-swell permeameter used for assessing volume changes during infiltration and drying, a hydraulic characterization permeameter used for characterizing the fluid retention curve and K-function for different materials, and a prototype permeameter used for modeling different soil profiles expected in the field. To ensure that the gravity forces are always acting downward on the specimen, the shrink/swell permeameter and the hydraulic characterization permeameter are swing-type permeameters. The permeameters are attached to a rotating rod that allows them to be vertical at 1-g and horizontal at N-g. Due to size constraints, the prototype permeameter is fixed horizontally. In addition, some details concerning the specific centrifuge and the data acquisition system are provided.

Figure 4A:
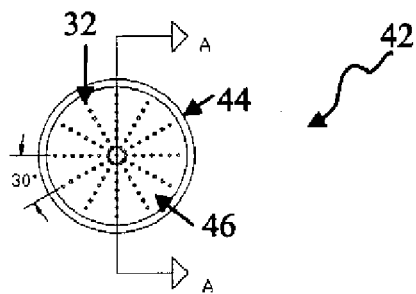
FIGS. 4A to 4H show the details of a swing-type CPUS shrink/swell permeameter.

Shrink/Swell Permeameter. FIG. 4 shows a shrink/swell permeameter. Wetting of soils and other porous materials may cause swelling. Similarly, drying of soils and other porous materials may cause shrinkage. FIG. 4A shows a top view of the shrink/swell permeameter 42. The shrink/swell permeameter 42 allows the change in height of a specimen to be measured during wetting and drying. The components of the shrink/swell permeameter 42 may include a cylinder 44. The cylinder 44 may be, for example a about 3 inch tall by about 2.5 inch inside diameter with about a 0.5 inch wall thickness; however, the dimensions may be modified depending on the specific application. The cylinder 44 may be made from acrylic, metal, plastic, polymers, resins or similar components. The cylinder 44 has a supporting disc 46 that rests on a shelf (not shown). The supporting disc 46 may have 1/32 inch holes with close spacing; however the holes may be between about 1/64 and about 1 inch. Furthermore, the holes do not need to be of a uniformed size over the surface and may be varies and alternated as needed.

Figure 4B:
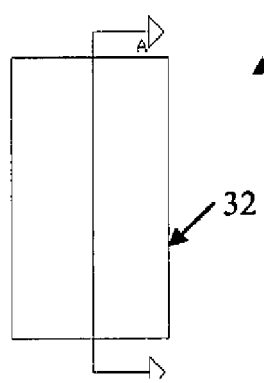
Figure 4E:
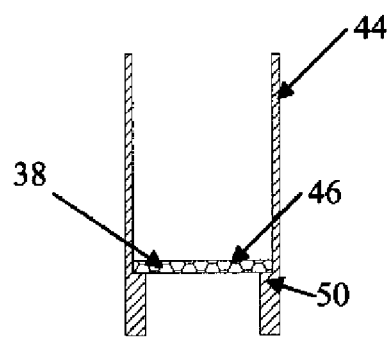
Figure 4C:
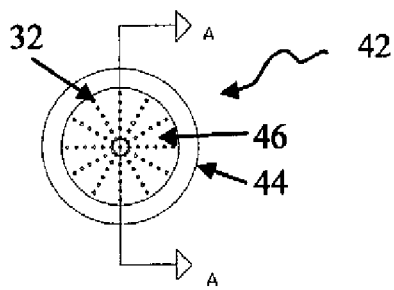

FIG. 4B shows an elevation view of the shrink/swell permeameter 42 illustrating the cylinder 44. FIG. 4C shows a bottom view of the shrink/swell permeameter 42. The components of the shrink/swell permeameter 42 may include a cylinder 44 and a supporting disc 46 that rests on a shelf (not shown). The supporting disc 46 may have 1/32 inch holes with close spacing; however the holes may be between about 1/64 and about 1 inch. Furthermore, the holes do not need to be of a uniform size over the surface and may be varied and alternated as needed. FIG. 4D shows a side view of the centrifuge holder 48 designed to fit the shrink/swell permeameter (not shown). FIG. 4E shows a cross sectional view of the shrink/swell permeameter 42. The components of the shrink/swell permeameter 42 may include a cylinder 44 and a supporting disc 46 that rests on a shelf 50. The supporting disc 46 may have a series of holes 38.

Figure 4F:
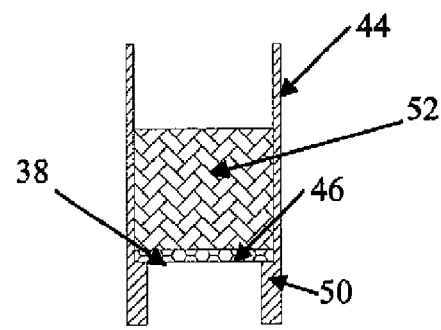
Figure 4D:
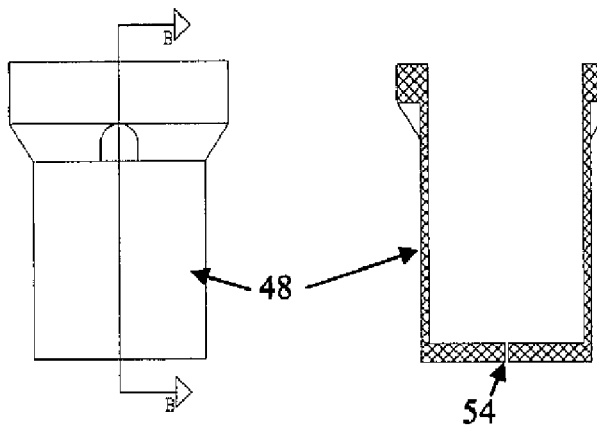
Figure 4G:
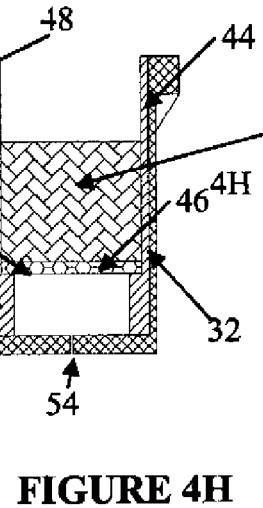

FIG. 4F shows a cross sectional view of the shrink/swell permeameter 42 having a sample placed therein. The components of the shrink/swell permeameter 42 may include a cylinder 44 and a supporting disc 46 that rests on a shelf 50. A sample of soil 52 is placed onto the supporting disc 46 having a series of holes 38. FIG. 4G shows a cross sectional view of the centrifuge holder 48 designed to fit the shrink/swell permeameter (not shown). The centrifuge holder 48 has one or more vents 54 positioned therein to allow for displacement.

Figure 4H:
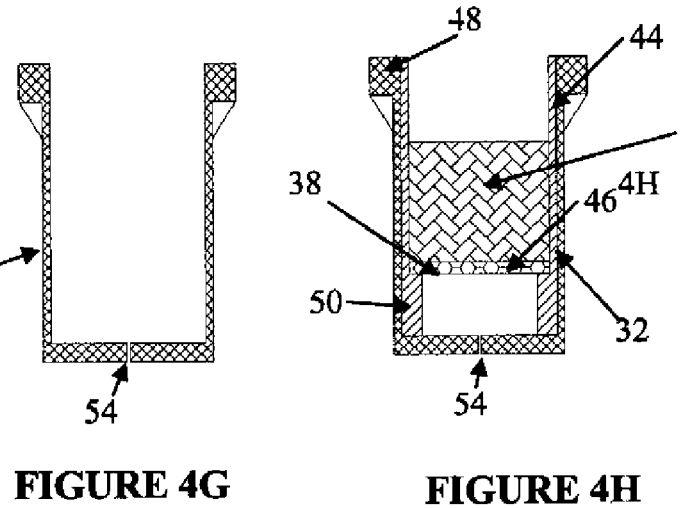

FIG. 4H shows a cross sectional view of the centrifuge holder 48 designed to fit the shrink/swell permeameter 42 having a sample 52 placed therein. The shrink/swell permeameter 42 includes a cylinder 44 and a supporting disc 46 that rests on a shelf 50. A sample of soil 52 is placed onto the supporting disc 46 having a series of holes 38. The centrifuge holder 48 has one or more vents 54 positioned therein to allow for displacement. The permeameter 42 is designed to fit in a centrifuge holder 48, which is designed to be supported within a centrifuge (not shown). Vacuum grease is applied onto the inside circumference of the cylinder to provide a low friction, low permeability boundary between a specimen and the cylinder.

A swelling test for the porous material in the shrink/swell permeameter may be conducted by: (i) placing a porous material into the permeameter cylinder, resting atop the support plate (ii) spinning the centrifuge to a selected rotational velocity, (ii) commencing fluid inflow by setting the infusion pump to a constant fluid flow rate, which causes fluid to flow through the rotary fluid union to the permeameter, (iii) observing the changes in specimen height during fluid inflow due to swelling, and (iv) measuring the changes in specimen weight. The height of the specimen may be measured visually, using a laser displacement transducer, or a linearly variable displacement transformer (LVDT). Similarly, after performing a swelling test, a shrinkage test for the porous material in the shrink/swell permeameter may be conducted by: (i) stopping fluid flow, (ii) observing the changes in specimen height during fluid outflow due to shrinkage, and (iii) measuring the changes in specimen weight. The moisture content of the specimen may be determined using an oven at the end of the test. The moisture content at different periods throughout the test may be back-calculated using the measured values of specimen weight. The changes in height during swelling and shrinkage may be correlated with the moisture content to determine volume changes during wetting and drying.

Figure 5A:
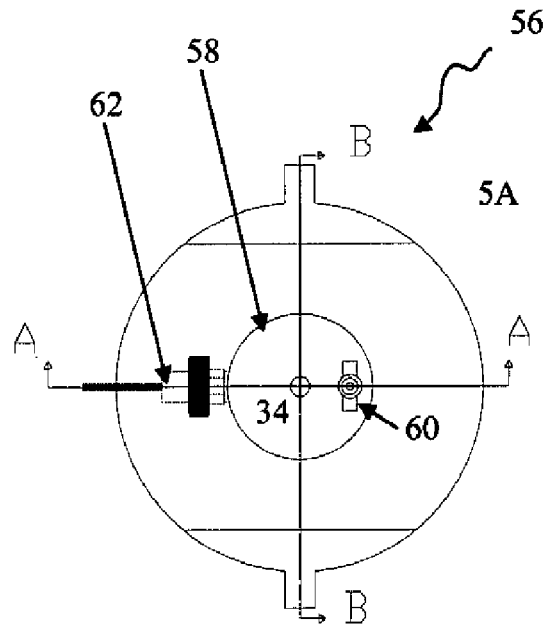
FIGS. 5A to 5C show the details of a swing-type CPUS hydraulic characterization permeameter.
Figure 5B:
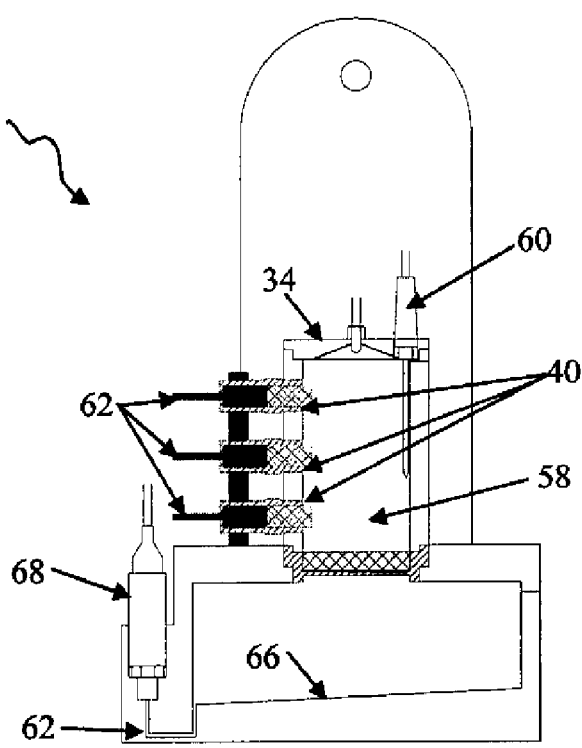
Figure 5C:
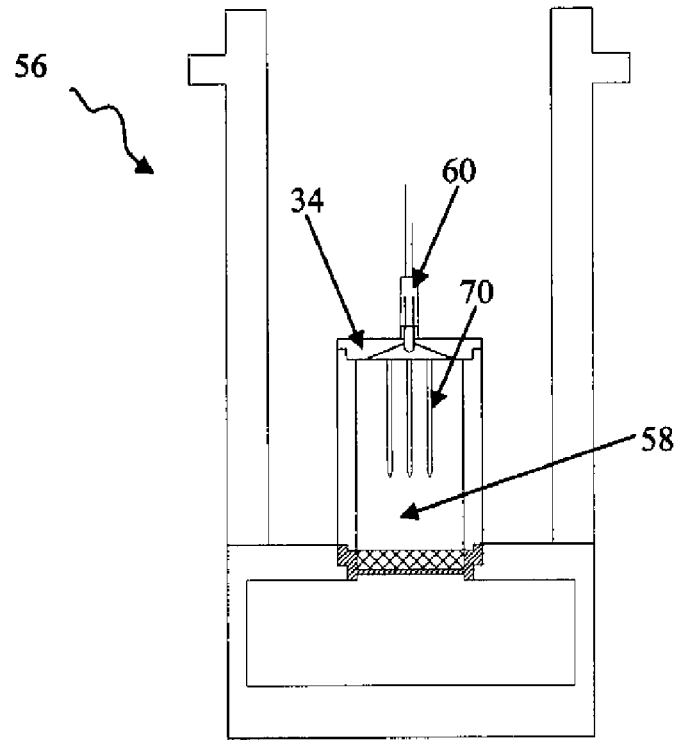

Hydraulic Characterization Permeameter. FIGS. 5A-5C show a hydraulic characterization permeameter 56. The characteristics of the hydraulic characterization permeameter 56 are the constant fluid inflow application system and continuous, in-flight measurement of suction, specimen moisture content, and fluid outflow. The hydraulic characterization permeameter 56 measures the transient suction, moisture content, and fluid flow rate profiles through the specimen. It is also used to define when steady-state fluid flow conditions have been achieved while in-flight in a centrifuge (not shown). This information may be used specifically to develop the relationships between the suction, moisture content and hydraulic conductivity.

FIG. 5A illustrates a top view of the hydraulic characterization permeameter 56. The hydraulic characterization permeameter 56 includes a cylinder 58 is fitted with a fluid inflow distribution cap 34 having a TDR probe 60. In communication with the cylinder 58 is one or more heat dissipation units 62. FIG. 5B show a cross sectional view of the hydraulic characterization permeameter 56. The hydraulic characterization permeameter 56 includes a cylinder 58 is fitted with a fluid inflow distribution cap 34 having a TDR probe 60. In communication with the cylinder 58 is one or more heat dissipation units 62 through the one or more ports 64. A outflow support disc 66 is positioned below the cylinder 58 and in communication with a fluid pressure transducer 42 (PT) to measure the volume of fluid outflow. FIG. 5C show another crossectional view of the hydraulic characterization permeameter 56. The hydraulic characterization permeameter 56 includes a cylinder 58 is fitted with a fluid inflow distribution cap 34 having a TDR probe 60. In communication with the cylinder 58 is one or more heat dissipation units 62. FIG. 5B show a cross sectional view of the hydraulic characterization permeameter 56. The hydraulic characterization permeameter 56 includes a cylinder 58 is fitted with a fluid inflow distribution cap 34 having a TDR probe 60. The TDR probe 60 extends into the cylinder 58 vertically along the side of the cylinder 58 to measure the average moisture content in the specimen (not shown), with the TDR prongs 48 embedded into the wall of the hydraulic characterization permeameter 56.

One embodiment of the hydraulic characterization permeameter 56 may be a cylinder 58 with dimensions of 3 inches tall with 2.5 inches inside diameter and a 0.5 inch wall thickness. The cylinder 58 may also have dimensions of between about 1-5 inches tall with between about 1-6 inches inside diameter and between about 0.25-1 inch wall thickness. The cylinder 58 is made from acrylic to prevent electrical interaction with the instrumentation; however other materials or coatings may be used in the fabrication of the cylinder 58, metals, alloys, plastics, polymers. In operation, fluid flow from an infusion pump (not shown) moves through the rotary fluid union (not shown) and enters the hydraulic characterization permeameter 56. Centripetal force generated by the spinning centrifuge (not shown) is used to accelerate fluid flow toward the distal portion of the hydraulic characterization permeameter 56. A fluid inflow distribution cap 34 may be provided with an o-ring seal (not shown) to the cylinder 58 (e.g., acrylic) to ensure even distribution of fluid over the specimen area. Placement of a pinhole (not shown) with a screw seal (not shown) allows air escape which prevents air pressure build-up during fluid inflow. The hydraulic characterization permeameter 56 may also have an outflow support disc 66, which may also include an o-ring seal to the permeameter cylinder 58 to prevent leakage. The outflow support disc 66 may be a 0.25 inch steel or acrylic plate with honeycomb mesh of $\frac{1}{32}$ inch holes; however the outflow support disc 66 may be between about 0.1 and 0.75 inches and constructed from metals, alloys, composites, polymers, plastics or similar materials and either coated partially, entirely or uncoated. A hole (not shown) beneath the support disc allows water to enter a primary outflow collection reservoir (not shown) without allowing fluid from flowing back into sample (not shown) when a centrifuge (not shown) is at rest. A primary fluid outflow collection reservoir includes one or more ports 62 for the placement of a fluid pressure transducer 68 (PT) used to measure the volume of fluid outflow. The collection reservoir is detachable for weighing. A pinhole with a screw seal (not shown) is provided to allow air escape (e.g., to prevent buildup of air pressure during fluid flow into the outflow collection reservoir), located on the upper side of the collection reservoir to prevent fluid leakage when centrifuge is at rest. One or more ports 62 are disposed along the cylinder 58 for instrumentation to allow heat dissipation units 64 to be in contact with the soil (not shown) to measure the suction distribution in the specimen (not shown). As seen in the cross-sectional insert of FIG. 5C, a TDR probe 60 is placed vertically along the side of the cylinder 58 to measure the average moisture content in the specimen (not shown), with the TDR prongs 70 embedded into the wall of the cylinder 58.

A typical test may be conducted in the hydraulic characterization permeameter 56 by: (i) spinning the centrifuge to a selected rotational velocity, (ii) commencing fluid inflow by setting the infusion pump (not shown) to a constant fluid flow rate, which causes fluid to flow through the rotary fluid union to the hydraulic characterization permeameter 56, (iii) observing the changes in suction and moisture content in the specimen while fluid advances through the specimen, (iv) measure the fluid outflow rate to determine when steady-state flow conditions occur. This procedure may be repeated at different rotational velocities and fluid flow rates to define different hydraulic properties. The fluid retention curve may be determined from the hydraulic characterization permeameter 56 of the CPUS system by plotting the values of the average suction and average moisture content measured during the test. The hydraulic conductivity function may be determined using the measured gradient in suction with specimen height and the fluid flow rate.

The hydraulic characterization permeameter 56 of the CPUS system can also be used for simpler tests, without instrumentation, to determine the relationship between the suction and moisture content. In this system, an initially fluid-saturated specimen rests upon a supporting plate, and is spun in the centrifuge (not shown) at a constant rotational velocity. Flow of fluid occurs from the base of the specimen until the conditions within the specimen are in equilibrium with the potential energy induced by the centrifuge (not shown). In fact, the potential energy induced by the centrifuge (not shown) can be thought of as an equivalent suction being imposed upon the specimen. After flow stops (i.e., equilibrium is reached), the specimen is weighed to determine the amount of moisture that has flowed out of the specimen. This procedure may be repeated in several stages, each with an increased centrifuge rotational velocity. After the final testing stage, the moisture content of the specimen may be determined using an oven, and the moisture content at each stage of the test may be back-calculated. A relationship between suction and moisture content can be determined to define the fluid retention curve.

Figure 6A:
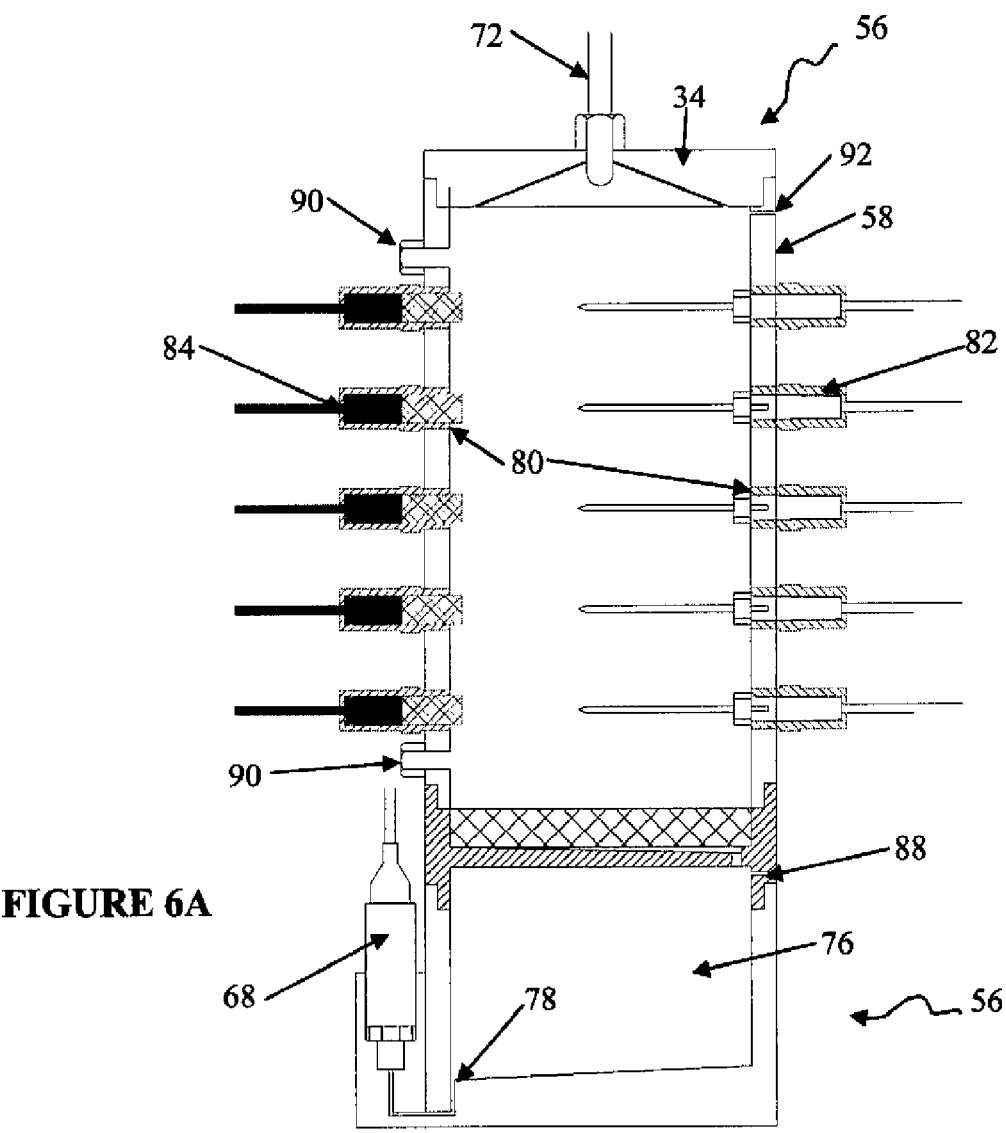
FIGS. 6A and 6B show the details of a stationary CPUS prototype permeameter.

Prototype Permeameter. FIG. 6 shows a cross sectional view of a prototype permeameter 70. Prototype is used to denote the scaled relationship between a small-scale specimen in the centrifuge and a large-scale earthen structure in the nature (e.g., dams, embankments, landfills, slopes, etc.). The prototype permeameter 70 is used to characterize the hydraulic properties of unsaturated soils as well as to model flow through unsaturated soil profiles with different depths. The prototype permeameter 70 has the additional capability of measuring and inducing evaporation from the upper surface of the specimen to simulate natural fluid flow processes. One embodiment of the prototype permeameter 70 has a cylinder 58, which may be 12 inches tall with 6 inches inside diameter and a 0.5 inch wall thickness. The inside height within the prototype permeameter is 12 inches with a soil specimen (not shown) height of about 11 inches, allowing for about 1 inch at the top for air space (not shown). However, the cylinder 58 may be between about 0.5 and 24 inches tall with between about 4 to 8 inches inside diameter and between about 0.25 and 1 inch wall thickness. The cylinder may be steel with an acrylic window for visualization (not shown).

In operation, fluid connection 72 from an infusion pump (not shown) moves through the rotary fluid union and enters the prototype permeameter 70. Centripetal force generated by the spinning centrifuge is used to accelerate fluid flow toward the distal portion 74 of the prototype permeameter 70. The prototype permeameter 70 has a fluid inflow distribution cap 34 to ensure even distribution of fluid over the soil surface (not shown). The fluid inflow distribution cap 34 may have an o-ring seal (not shown) to the cylinder 58 to prevent fluid leakage. The cylinder 58 may have air ports (not shown) for air entry and air escape (e.g., two 0.25 inch NPT holes at a height of 11.5 inches from the base of the permeameter) to induce evaporation from the top surface of the soil sample (not shown). An outflow support disc 66 may be made from 0.5 inch steel or acrylic disc with honeycomb mesh of 1/32 inch holes, which may also be sealed with an o-ring seal (not shown) to the cylinder 58 to prevent fluid leakage. However the outflow support disc 66 may be between about 0.1 and 0.75 inches with a honeycomb mesh of between 1/64 and 1 inch holes and constructed from metals, alloys, composites, polymers, plastics or similar materials and either coated partially, entirely or uncoated.

The prototype permeameter 70 has an external primary fluid outflow collection reservoir(s) 76, with use of a fluid pressure transducer 68 (PT) to measure the pressure in the fluid within the fluid outflow collection reservoir(s) 76. A hole beneath the support disc (not shown) allows water to enter a primary outflow collection reservoir 76 without allowing fluid from flowing back into sample ((not shown) when a centrifuge (not shown) is at rest. A primary fluid outflow collection reservoir 76 includes one or more ports 78 for the placement of a fluid pressure transducer (PT) 68 used to measure the volume of fluid outflow. The fluid outflow collection reservoir 76 is detachable for 1-g weighing. The primary outflow collection reservoir 76 may be connected to a secondary expansion outflow collection reservoir (not shown). One or more secondary expansion outflow collection reservoir(s) (not shown) allows overflow from the primary outflow collection reservoir 76 for extended testing and may be located adjacent to the primary outflow collection reservoir 76.

Figure 6B:
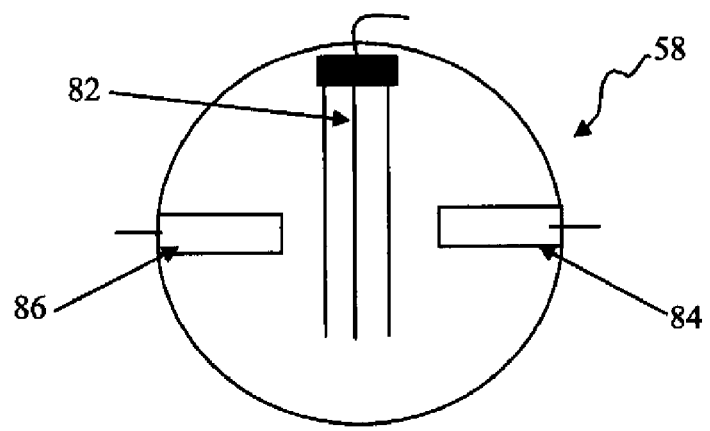

The prototype permeameter 70 includes a number of instrumentation holes (not shown). In one embodiment, e.g., a total of 18 holes (e.g., 0.5 inch NPT) are placed along the cylinder 58. For example, the 18 holes may include 3 circumferentially spaced arrays of 5 equally spaced vertical holes. In one example, arrays ports 80 include 3 arrays of 5 ports (e.g., 2 inch spacing from the bottom of the permeameter) are used. The arrays ports 80 will be used for heat dissipation units 84, time domain reflectometry probes (not shown), and other instrumentation (e.g., tensiometers, temperature, etc.) (not shown). For example, typical TDR probe are 4.5 inches long, HDUs are 2.5 inches long, and tensiometers are 1 inch long, so the probes will be close to each other. Because of the close spacing, the vertical profiles may be placed at, e.g., 0 degrees, 90 degrees, and 180 degrees, with the TDR probe 82 in the center and the HDU 84 and tensiometers 86 perpendicular as shown in FIG. 6B.

Additionally, the cylinder 90 may have a pinhole with a screw seal 88 is provided to allow air escape (e.g., to prevent buildup of air pressure during fluid flow into the outflow collection reservoir) and a vent hole 88 located on the upper side of the collection reservoir to prevent fluid leakage when centrifuge is at rest.

One or more fluid level holes may be placed at a height of 1 inch from the base, spaced 120 degrees circumferentially. The fluid level holes may be used as an alternate boundary condition consisting of a fluid level maintained constant at the specimen base. A plug 78 in the bottom of the fluid outflow collection reservoir(s) 76 allows fluid to accumulate in the specimen to the level of the fluid level holes. Fluid may then spill over through the fluid level holes (not shown) into the outflow collection cylinder (not shown).

One or more air flow holes 80 may also be included made for air flow, e.g., one for air inlet and the other for air outlet. The air flow hole 92 may be located at a height of 11 inches above the top of the soil layer. The prototype permeameter 70 may also include a number of mounting points (not shown) which allow the prototype permeameter 70 to be mounted into the centrifuge (not shown). For sample visualization, one or more windows (e.g., acrylic) in upper channel of the drum may be included (not shown). To obtain images of the sample during flow, one or more strobe lights (not shown) timed to the rotational velocity of the centrifuge (not shown) may be positioned to visualize the sample in-flight. For example, a charge-coupled display (CCD) camera may be used for visualization.

A typical test in the prototype permeameter test may be conducted using a procedure similar to that of the hydraulic characterization permeameter. The main differences would be the selection of a rotational velocity in the centrifuge (not shown) such that scaling relationships can be used to correlate the behavior of the specimen (model) to an equivalent earthen structure in the field (prototype). Different from the hydraulic characterization permeameter 56, inflow may be stopped and evaporation may be induced by passing air through the air ports at the top of the prototype permeameter 70. This will create an upward flow of water, which may be monitored using the heat dissipation units (not shown) and time domain reflectometry probes (not shown). Accordingly, infiltration and evaporation may be controlled to simulate weather processes that may affect an earthen structure in the field.

FIGS. 7A-F show different permeameter configurations in a centrifuge 94. FIGS. 7A and 7B show top views of a prototype permeameter hanger 96 and of a characterization or shrink/swell permeameter environments 98 inside a centrifuge 94, respectively. FIGS. 7C and 7D show elevation views of a prototype permeameter hanger 96 and a characterization or shrink/swell permeameter environments 98 inside a centrifuge 94, respectively. FIGS. 7E and 7F show isometric views of a prototype permeameter 96 and a shrink/swell permeameter environments 98 inside a centrifuge 94, respectively.

The TDR cable tester and multiplexer (not shown) may be placed in the center of the centrifuge 94. A data acquisition system (not shown) within the centrifuge 94 is connected to the probes (not shown) and or detection devices (not shown) placed along the permeameters to detect the following variables: moisture content; suction; fluid inflow rate; fluid outflow rate (e.g., to verify steady-state fluid flow conditions); specimen weight (e.g., to measure evaporation); air temperature or relative humidity; and/or specimen temperature. To measure these variables a number of instruments are used. For example, time domain reflectometry to measure moisture content (including a holding device for a cable tester and multiplexer); heat dissipation units to measure suction (e.g., 4 for each permeameter); tensiometers to measure suction (e.g., 4 for each permeameter); thermocouple psychrometers to measure suction (e.g., 4 for each permeameter); pressure transducer to measure fluid outflow rate measurement (e.g., 1 for each permeameter); an electronic load cell or pressure transducer to measure measuring specimen weight (e.g., 2 for each permeameter); a linearly variable displacement transformer to measure settlement measurements in the shrink/swell permeameter (e.g., 1 for each permeameter); and/or thermocouples to measure specimen and air temperatures (e.g., 3 for each permeameter). In this configuration, the data acquisition device uses at least 32 channels and is capable of interacting with cable-tester software. A power supply in the centrifuge 94 is provided for all transducers between 5 and 30 volts for operation, except for the TDRs (not shown). Although this embodiment uses 32 channels other embodiments may use different numbers of channels, e.g., 8, 16, 48 etc.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain components which are both chemically and physiologically related may be substituted for the components described herein while the same or similar results would be achieved. All such similar substitutes and modifications apparent to those skilled in the art are deemed to be within the spirit, scope and concept of the invention as defined by the appended claims.

What is claimed is:

1. A method of measuring unsaturated soil characteristics comprising the steps of:
   placing a soil specimen in a centrifuge permeameter;
   applying a centripetal acceleration to the soil specimen;
   applying a low-flow rate to at least one portion of the soil specimen during centrifugation;
   controlling an outflow boundary condition within the centrifuge permeameter to generate an open-flow boundary condition; and
   continuously measuring one or more characteristics of the soil specimen while in flight.

2. The method of claim 1, wherein the centripetal acceleration applied to the soil specimen is selected to permit a suction and a moisture content to attain equilibrium with an ongoing flow.

3. The method of claim 1, wherein open-flow and outflow boundary conditions in the centrifuge permeameter are selected to permit the suction and moisture content to attain any value in equilibrium with the ongoing flow processes.

4. The method of claim 1, wherein the centrifuge permeameter continuously measures the variables relevant to unsaturated fluid flow through soils while the centrifuge is in flight.

5. The method of claim 1, wherein a centrifuge permeameter instrumentation continuously measures one or more characteristics selected from an unsaturated soil specimens: moisture content, suction temperature, fluid inflow rate, fluid outflow rate, steady-state fluid flow, specimen weight, evaporation and combinations thereof.

6. The method of claim 1, wherein the one or more characteristics are used in geotechnical engineering, hydrology, agriculture, environmental engineering and petroleum engineering.

7. The method of claim 1, further comprising the step of applying heat to the soil specimen to induce moisture evaporation while continuously and nondestructively measuring relevant variables such as the change in temperature, relative humidity, and small changes in the weight of a soil specimen while in flight.

* * * * *

UNITED STATES PATENT AND TRADEMARK OFFICE
CERTIFICATE OF CORRECTION

| | | |
|---|---|---|
| PATENT NO. | : 7,367,218 B2 | Page 1 of 1 |
| APPLICATION NO. | : 11/563052 | |
| DATED | : May 6, 2008 | |
| INVENTOR(S) | : Zornberg et al. | |

It is certified that error appears in the above-identified patent and that said Letters Patent is hereby corrected as shown below:

On the Title Page, Item (62), the cross reference "of application No. 11/536,053, filed on Nov. 24, 2006, and a division" should be deleted. Leaving "Division of application No. 11/297,261, filed on Dec. 8, 2005".

Column 1, lines 12-13, the phrase "and Divisional Application U.S. patent application Ser. No. 11/563/053, also filed Nov. 24, 2006" should be deleted.

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,367,218 B2 | Page 1 of 1 |
| APPLICATION NO. | : 11/563052 | |
| DATED | : May 6, 2008 | |
| INVENTOR(S) | : Jorge G. Zornberg and John S. McCartney | |

It is certified that error appears in the above-identified patent and that said Letters Patent is hereby corrected as shown below:

Col. 1, line 16
Replace "government may own certain rights in this invention" with --government has certain rights in this invention--

Signed and Sealed this

Ninth Day of February, 2010

David J. Kappos
*Director of the United States Patent and Trademark Office*